US012377123B2

(12) United States Patent
Ta

(10) Patent No.: US 12,377,123 B2
(45) Date of Patent: Aug. 5, 2025

(54) PREOPERATIVE COMPOSITIONS AND METHODS OF PREPARATION THEREOF

(71) Applicant: Thi Tuyet Mai Ta, Kent, WA (US)

(72) Inventor: Thi Tuyet Mai Ta, Kent, WA (US)

(73) Assignee: PREOPERATIVE NUTRITION, Kent, WA (US)

( * ) Notice: Subject to any disclaimer, the term of this patent is extended or adjusted under 35 U.S.C. 154(b) by 0 days.

(21) Appl. No.: 17/560,060

(22) Filed: Dec. 22, 2021

(65) Prior Publication Data

US 2022/0193154 A1 Jun. 23, 2022

Related U.S. Application Data

(63) Continuation-in-part of application No. 17/331,613, filed on May 26, 2021, now abandoned.

(60) Provisional application No. 63/130,348, filed on Dec. 23, 2020.

(51) Int. Cl.

| | |
|---|---|
| ***A61K 35/745*** | (2015.01) |
| ***A61K 31/015*** | (2006.01) |
| ***A61K 31/07*** | (2006.01) |
| ***A61K 31/122*** | (2006.01) |
| ***A61K 31/355*** | (2006.01) |
| ***A61K 31/375*** | (2006.01) |
| ***A61K 31/593*** | (2006.01) |
| ***A61K 33/04*** | (2006.01) |
| ***A61K 33/06*** | (2006.01) |
| ***A61K 33/26*** | (2006.01) |
| ***A61K 33/30*** | (2006.01) |
| ***A61K 35/20*** | (2006.01) |
| ***A61K 35/744*** | (2015.01) |
| ***A61K 35/747*** | (2015.01) |
| ***A61K 36/48*** | (2006.01) |
| ***A61K 47/14*** | (2017.01) |
| ***A61K 47/26*** | (2006.01) |
| ***A61P 41/00*** | (2006.01) |

(52) U.S. Cl.

CPC .......... *A61K 35/745* (2013.01); *A61K 31/015* (2013.01); *A61K 31/07* (2013.01); *A61K 31/122* (2013.01); *A61K 31/355* (2013.01); *A61K 31/375* (2013.01); *A61K 31/593* (2013.01); *A61K 33/04* (2013.01); *A61K 33/06* (2013.01); *A61K 33/26* (2013.01); *A61K 33/30* (2013.01); *A61K 35/20* (2013.01); *A61K 35/744* (2013.01); *A61K 35/747* (2013.01); *A61K 36/48* (2013.01); *A61K 47/14* (2013.01); *A61K 47/26* (2013.01); *A61P 41/00* (2018.01)

(58) Field of Classification Search

CPC .... A61K 35/745; A61K 31/015; A61K 31/07; A61K 31/122; A61K 31/355; A61K 31/375; A61K 31/593; A61K 33/04; A61K 33/06; A61K 33/26; A61K 33/30; A61K 35/20; A61K 35/744; A61K 35/747; A61K 36/48; A61K 47/14; A61K 47/26; A61K 31/23; A61K 31/7004; A61K 31/718; A61K 31/733; A61K 35/741; A61K 38/1709; A61P 41/00; A23L 33/135; A23L 33/15; A23L 33/185; A23L 33/19

See application file for complete search history.

(56) References Cited

U.S. PATENT DOCUMENTS

| | | | | |
|---|---|---|---|---|
| 9,283,263 | B2 * | 3/2016 | Westerlund | A61K 31/4415 |
| 9,616,094 | B2 * | 4/2017 | Schiffrin | A61P 37/02 |
| 2014/0294788 | A1 * | 10/2014 | Bailey | A23L 33/40 424/93.42 |
| 2015/0201635 | A1 * | 7/2015 | Graf | A23C 9/1542 426/74 |
| 2017/0056339 | A1 * | 3/2017 | Aukrust | A23P 10/35 |

FOREIGN PATENT DOCUMENTS

| | | | | |
|---|---|---|---|---|
| CN | 111165825 | * | 5/2020 | A23L 33/125 |
| WO | WO 2016/044272 | * | 3/2016 | |

OTHER PUBLICATIONS

Walpole, S. C., Prieto-Merino, D., Edwards, P., Cleland, J., Stevens, G., & Roberts, I. (2012). The weight of nations: an estimation of adult human biomass. BMC public health, 12(1), 1-6. (Year: 2012).*

Hirsch, K. R., Wolfe, R. R., & Ferrando, A. A. (2021). Pre-and post-surgical nutrition for preservation of muscle mass, strength, and functionality following orthopedic surgery. Nutrients, 13(5), 1675. (Year: 2021).*

Lederer, A. K., Pisarski, P., Kousoulas, L., Fichtner-Feigl, S., Hess, C., & Huber, R. (2017). Postoperative changes of the microbiome: are surgical complications related to the gut flora? A systematic review. BMC surgery, 17(1), 1-10. (Year: 2017).*

Translation of Zhang (May 2019) CN111165825A Retrieved on Dec. 15, 2022 from (https://worldwide.espacenet.com/patent/search/family/070617888/publication/CN111165825A?q=pn%3DCN111165825A) (Year: 2020).*

Kelly, J., Kelly, P. M., & Harrington, D. (2002). Influence of processing variables on the physicochemical properties of spray dried fat-based milk powders. Le Lait, 82(4), 401-412. (Year: 2002).*

(Continued)

*Primary Examiner* — Melenie L Gordon

*Assistant Examiner* — Kimberly C. Breen

(74) *Attorney, Agent, or Firm* — FULLER IP LAW LLC; Rodney J. Fuller

(57) ABSTRACT

Disclosed are preoperative compositions and methods of preparation thereof. The preoperative compositions may be for minimizing thirst, vomiting, insulin resistance, and the like prior to surgery. Such preoperative compositions may also reduce postoperative complications and the need for pain relievers, as well as minimize blood transfusion needed during and after surgery when administered the night before the operation and/or an hour before the operation. The preoperative compositions may include soy milk, isolate milk protein, isolate pea proteins, probiotics, whole milk powder, and micronutrients for example.

11 Claims, 6 Drawing Sheets

(56) References Cited

OTHER PUBLICATIONS

Dock-Nascimento, D. B., de Aguilar-Nascimento, J. E., Magalhaes Faria, M. S., Caporossi, C., Slhessarenko, N., & Waitzberg, D. L. (2012). Evaluation of the effects of a preoperative 2-hour fast with maltodextrine and glutamine on insulin resistance, acute-phase response, nitrogen balance, (Year: 2012).*

Dock-Nascimento citation continued) and serum glutathione after laparoscopic cholecystectomy: a controlled randomized trial. Journal of Parenteral and Enteral Nutrition, 36(1), 43-52. (Year: 2012).*

Calbrix, M. (Apr. 15, 2022). What is demineralized whey ? Armor-Proteines. https://blog.armor-proteines.com/en/what-is-demineralized-whey (Year: 2022).*

Mizobe, T., Nakajima, Y., Ueno, H., & Sessler, D. I. (2006). Fructose administration increases intraoperative core temperature by augmenting both metabolic rate and the vasoconstriction threshold. The Journal of the American Society of Anesthesiologists, 104(6), 1124-1130. (Year: 2006).*

Rayes, N., Hansen, S., Seehofer, D., Müller, A. R., Serke, S., Bengmark, S., & Neuhaus, P. (2002). Early enteral supply of fiber and Lactobacilli versus conventional nutrition: a controlled trial in patients with major abdominal surgery. Nutrition, 18(7-8), 609-615. ( Year: 2002).*

Orion Infusion Ltd. (n.d.). Www.orioninfusion.com; Orion Infusion. Retrieved Apr. 1, 2024, from https://www.orioninfusion.com/fructose.php#:~: text=Fructose%2D10%20is%20used%20intravenously (Year: 2024).*

"Merriam-Webster Dictionary." Merriam-Webster.com, 8 Sep. 2024, www.merriam-webster.com/dictionary/evening. Accessed Sep. 18, 2024. (Year: 2024).*

Perrone, Francine, et al. "Effects of preoperative feeding with a whey protein plus carbohydrate drink on the acute phase response and insulin resistance. A randomized trial." Nutrition journal 10 (2011): 1-7. (Year: 2011).*

Smith-Ryan, A. E., Hirsch, K. R., Saylor, H. E., Gould, L. M., & Blue, M. N. (2020). Nutritional considerations and strategies to facilitate injury recovery and rehabilitation. Journal of Athletic Training, 55(9), 918-930. (Year: 2020).

Rubin Institute for Advanced Orthopedics (referred to as RIAO) (2019) "Fasting Requirements Before Surgery", Lifebridge Health. Retrieved on Dec. 15, 2022, from https://www.limblength.org/wp-content/uploads/2019/05/Fasting-Requirements-Before-Surgery.pdf ( Year: 2019).

Ramouz, A., Hosseini, M., Hosseinzadeh, S. S., & Rasihashemi, S. Z. (2020). Preoperative Vitamin D supplementation in patients with Vitamin D deficiency undergoing total thyroidectomy. The American Journal of the Medical Sciences, 360(2), 146-152. (Year: 2020).

Del Piano, M., Carmagnola, S., Andorno, S., Pagliarulo, M., Tari, R., Mogna, L., & Capurso, L. (2010). Evaluation of the intestinal colonization by microencapsulated probiotic bacteria in comparison with the same uncoated strains. Journal of clinical gastroenterology, 44, S42-S46. (Year: 2010).

Balzer C, Raackow D, Hahnenkamp K, Flessa S, Meissner K. (2017). Timeliness of Operating Room Case Planning and Time Utilization: Influence of First and To-Follow Cases. Frontiers in Medicine. 4:DOI=10.3389/fmed.2017.00049.

Braga M, Gianotti L, Vignali A, Carlo VD. (2002) Preoperative oral arginine and n-3 fatty acid supplementation improves the immunometabolic host response and outcome after colorectal resection for cancer. Surgery. 2002;132 (5):805-814. doi:10.1067/msy.2002.128350.

Cordeiro BF, Oliveira ER, da Silva SH, Savassi BM, Acurcio LB, Lemos L, Alves JL, Assis HC, Vieira AT, Faria AMC, Ferreira E, Le Loir Y, Jan G, Goulart LR, Azevedo V, Carvalho RDO and do Carmo FLR (2018) Whey Protein Isolate-Supplemented Beverage, Fermented by Lactobacillus casei BL23 and Propionibacterium freudenreichii 138, in the Prevention of Mucositis in Mice. Front. Microbiol. 9:2035. doi: 10.3389/fmicb.2018.02035.

* cited by examiner

PREOPERATIVE COMPOSITIONS AND METHODS OF PREPARATION THEREOF

CROSS-REFERENCE TO RELATED APPLICATION

This application is a continuation-in-part of U.S. patent application Ser. No. 17/331,613 filed on May 26, 2021, which claims the benefit of the filing date of U.S. Provisional Patent Application 63/130,348 entitled "PREOPERATIVE COMPOSITIONS AND METHODS OF PREPARATION THEREOF" to Ta Thi Tuyet Mai that was filed on Dec. 23, 2020, the disclosures of each of which are hereby incorporated by this reference.

TECHNICAL FIELD

The present disclosure relates to preoperative compositions and methods of preparation thereof, and more specifically to preoperative compositions for administration to a patient at about 6 AM the day of surgery or about 2 hours before surgery to both prepare for the medical procedure and to aid recovery from the procedure.

BACKGROUND

Traditionally and for decades, patients have been mandated to fast the night before a surgery. The common fasting periods of 6 to 8 hours and sometimes as long as 10 to 12 hours aggravate insulin resistance, which is a marker of surgical stress. Currently, the American Anesthesia Association allows oral fluids up to 2 hours before surgery. On the other hand, the European Association for Clinical Metabolism and Nutrition recommends drinking sugar water two hours before administration of anesthesia. Unfortunately, these outdated practices persist despite emerging evidence revealing that excessive fasting results in negative outcomes and delayed recovery.

Many clinical studies have demonstrated preoperative carbohydrate loading can be reduce insulin resistance and increase postoperative patient satisfaction (for example, reducing thirst, nausea, and vomiting). Gastric contents that are considered to increase the risk of aspiration pneumonitis in anesthesia are a pH less than 2.5 and gastric volume of 0.4 ml/kg; but the preoperative dose of carbohydrates did not affect the preoperative gastric storage volume and pH, so giving carbohydrate beverages to the patients before surgery has become an essential step in the postoperative early recovery program (ERAS).

However, the current practice is not suitable for all patients. Most studies in the world have been performed on patients of European descent (in Europe and the United States), where patients were told to drink 800 ml of a solution containing 12.5% by weight the night before surgery and 400 ml of the same solution two hours before surgery. These volumes are relatively large compared to patients of Asian descent. For example, hospitals in Vietnam have not implemented the ERAS, because the anesthetist refuses to give local patients such a large volume of liquids before surgery. Accordingly, alternative solutions are needed where a smaller volume of preoperative solution could be administered without reducing its beneficial effects on insulin responsiveness, nausea and vomiting, and sensation of thirst.

SUMMARY

Aspects of this document relate to preoperative compositions that improve patient outcomes and postoperative satisfaction when administered the evening before and in some implementations at about 6 AM the day of surgery or at least 2 hours before surgery.

A preoperative composition may include a soy milk, isolate milk protein, isolate pea protein, a composition of probiotic organisms, and a composition of vitamins and minerals.

Implementations may include one or more or all of the following.

The composition of probiotic organisms may include at least one species of bacteria selected from the group consisting of: *Lactobacillus acidophilus, Lactobacillus reuteri, Lactobacillus casei, Bifidobacterium longum*, and *Streptococcus faecalis*. For example, the composition of probiotic organisms may include *L. acidophilus; L. reuteri; L casei; B. longum*; and *S. faecalis*. The composition of probiotic organisms may be microencapsulated. The composition of probiotics may only be added into the nutritional composition prior to oral ingestion.

The composition of vitamins and minerals may include selenium and vitamin K2. The composition of vitamins and minerals may further include at least one vitamin or mineral selected from the group consisting of: retinol, carotene vitamin E, vitamin D, vitamin K1, a vitamin B, vitamin C, iron, magnesium, and zinc. Vitamin D may be vitamin D3. Vitamin B may be thiamin, riboflavin, niacin, vitamin B6, vitamin B7, vitamin B9, vitamin B12, or a combination thereof. The composition of vitamins and minerals may be microencapsulated.

The isolate milk protein may be at least partially provided by whole milk powder. The whole milk powder may be unsweetened. The isolate milk protein may be at least partially provided by demineralized whey powder.

The percent by weight of the isolate milk protein may be at least 3.3% (w/v). The percent by weight of the isolate milk protein may be 2.9-3.8% (w/v).

The percent by weight of the unsweetened whole milk powder may be at least 8.6% (w/v). The percent by weight of the whole milk powder may be between 8-9% (w/v).

The percent by weight of the isolate pea protein may be at least 2.4% (w/v). The percent by weight of the isolate pea protein may be 2.1-2.7% (w/v).

The percent by weight of soy milk may be at least 72.2% (v/v). The percent by weight of soy milk may be between 70-75% (v/v).

The percent by weight of the isolate milk protein may be at least 10.8% (w/w). The percent by weight of the isolate milk protein may be 9.3-12.8% (w/w).

The percent by weight of the isolate pea protein may be at least 7.8% (w/w). The percent by weight of the isolate pea protein may be 6.7-9.2% (w/w).

The percent by weight of instant soy milk powder may be at least 12.4% (w/w). The percent by weight of instant soy milk powder may be 10.7-14.7% (w/w).

The percent by weight of unsweetened whole milk powder may be at least 18.9% (w/w). The percent by weight of unsweetened whole milk powder may be 16.3-22.4% (w/w).

The preoperative composition may further include a medium chain triglyceride. The percent by weight of the medium chain triglyceride may be between 2-3% (w/v).

The preoperative composition may further include a sugar. The percent by weight of the sugar may be 1.8-4% (w/v) or 6-13% (w/w). The sugar may be fructose, inulin, or a combination thereof.

The preoperative composition may also include a sugar solution comprising 25% by weight sugar. The sugar provided by the sugar solution may be glucose, for example in the form of maltodextrin.

At least 20% of the protein content of the preoperative composition may be branched-chain amino acids.

Other aspects of this disclosure relate to methods of preparing a patient for surgery that may include administering to the patient the nutritional composition the evening before the surgery (e.g., at least six (6) hours prior to surgery), or may include administering to the patient the nutritional composition the evening before the surgery and then administering to the patient a sugar solution at about 6 AM the morning prior to surgery (e.g., at least two hours prior to the surgery or between two to four hours prior to the surgery). In some implementations, the sugar solution is administered to the patient at 4.4±2.1 hours prior to surgery. That way the patient ingests nothing in addition to the nutritional composition, the sugar solution, and water for at least six (6) hours prior to the surgery Regardless of the particular method of preparing a patient for surgery, the nutritional composition may include soy milk; isolate milk protein; isolate pea protein; a composition of probiotic organisms; and a composition of vitamins and minerals comprising selenium and vitamin K2.

Implementations may include one or more or all of the following.

The sugar solution may include 25% by weight maltodextrin.

The sugar solution may provide 50 g maltodextrin.

The sugar solution may provide between 0.7-1.3 g sugar/kg body weight of the patient.

The nutritional composition may provide:

- 0.2±0.06 g isolate milk protein/kg body weight of the patient;
- 0.1±0.04 g isolate pea protein/kg body weight of the patient;
- 4.1±1.3 μg selenium/kg body weight of the patient; and/or
- 7.4±2.4 μg vitamin K2/kg body weight of the patient.

The nutritional composition may provide:

- 0.2±0.1 g isolate milk protein/kg body weight of the patient;
- 0.1±0.5 g isolate pea protein/kg body weight of the patient;
- 4.1±2.1 μg selenium/kg body weight of the patient; and/or
- 7.4±3.7 μg vitamin K2/kg body weight of the patient.

The nutritional composition may provide 0.08±0.02 g branched-chain amino acid/kg body weight of the patient.

The patient may be administered the nutritional composition between 6-12 hours prior to the surgery.

The patient may be administered the nutritional composition one evening before the surgery and the sugar solution at 6:00 AM on the surgery day.

The patient may be orally administered the nutritional composition and the sugar solution.

Still other aspects of this disclosure relate to methods of producing shelf-stable forms of the nutritional composition and the sugar solution.

The foregoing and other aspects, features, and advantages will be apparent to those of ordinary skill in the art from the specification, drawings, and the claims.

BRIEF DESCRIPTION OF THE DRAWINGS

Implementations will hereinafter be described in conjunction with the appended drawings, where like designations denote like elements.

DETAILED DESCRIPTION

Figure 1A:
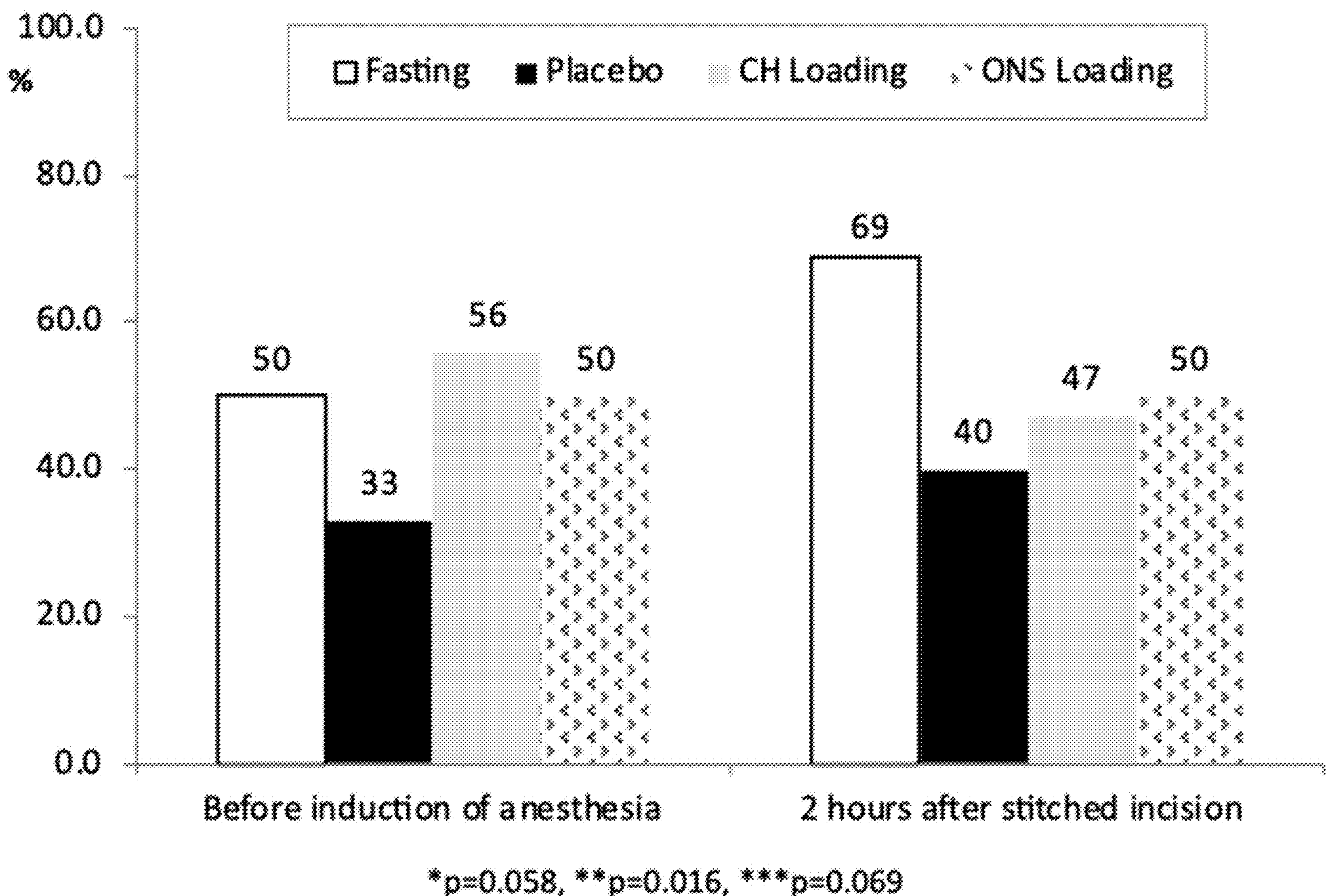
FIG. 1A depicts, in accordance with certain implementations, the percentage of patients in four groups who were determined by the Homeostasis Model Assessment to have insulin resistance before administration of anesthesia and two after stitched incision (percentage of patients, who had HOMA-IR ⩾ 2.5, before induction of anesthesia and 2 hours after stitched incision). Group 1 patients fasted prior to their surgery ("Fasting"). Group 2 patients drank only a placebo composition (aspartame 0.035%, 400 mL) the night before their surgery and another dose of the placebo composition (aspartame 0.035%, 200 mL) at 6:00 AM on their operation day ("Placebo"). Group 3 patients drank 400 ml of a composition comprising Maltodextrin 25% the night before their surgery followed by 200 ml of the same composition at 6:00 AM on their operation day ("CH Loading"). Group 4 patients drank the 300 ml of the disclosed nutritional composition the night before their surgery and 200 ml of the disclosed sugar solution at 6:00 AM on their operation day ("ONS Loading"). *p, significant difference levels between 4 groups were calculated by Chi-Square test (p*)

While this disclosure includes a number of implementations that are described in many different forms, there is shown in the drawings and will herein be described in detail particular implementations with the understanding that the present disclosure is to be considered as an exemplification of the principles of the disclosed compositions and methods and is not intended to limit the broad aspect of the disclosed concepts to the implementations illustrated.

In the following description, reference is made to the accompanying drawings which form a part hereof, and which show by way of illustration possible implementations. It is to be understood that other implementations may be utilized, and component, as well as procedural, changes may be made without departing from the scope of the present disclosure. As a matter of convenience, various compositions and methods will be described using exemplary specifications, amounts, ranges, steps, procedures, and the like.

However, this document is not limited to the stated examples and other compositions and methods are possible and within the teachings of the present disclosure. As will become apparent, changes may be made in the function, use, and/or arrangement of any of the components and steps described in the disclosed exemplary implementations without departing from the spirit and scope of this disclosure.

In the following description, and for the purposes of explanation, numerous specific details are set forth in order to provide a thorough understanding of the various aspects of the present disclosure. It will be understood, however, by those skilled in the relevant arts, that the present disclosure may be practiced without these specific details. It should be noted that there are many different and alternative compositions, methods, configurations, devices and technologies to which the present disclosure may be applied. The full scope of the present disclosure is not limited to the examples that are described below.

Described herein are nutritional compositions for administration the night before surgery and sugar solutions for administration at 6 AM of day surgery or at least two hours before surgery, where the administration of the compositions facilitates postoperative recovery in the patient, including recovery from general anesthesia. In some aspects, the sugar solution is administered about 3 hours prior to surgery for a diabetic patient. In other aspects, the sugar solution is administered about 4.4±2.1 hours prior to surgery. Also described is a method of preparing a patient for surgery comprising administering to the patient a nutritional composition described herein the night before the surgery and then administering to the patient a sugar solution described herein at least two hours before surgery. In certain implementations, the sugar solution is administered to the patient at 6:00 AM on the day of surgery.

The administration of such compositions to the patient according to methods described herein reduces the patient's thirst, incidence of vomiting, insulin resistance, complications after surgery. As shown in the examples, the Comprehensive Complication Index of patients given the nutritional composition the night before the surgery and then the sugar solution 4.4±2.1 hours prior to surgery or 6 AM on the day of surgery (referred to herein as "the intervention group") was only 29.6±4.2 compared to a patient who just fasted before surgery (referred to herein as "the fasting group"), 45.2±4.5, $p<0.05$. The mean of postoperative morbidity survey of the intervention group was lower than that of the fasting group, 1.7±0.2 compared with 2.6±0.2, $p<0.05$.

In some aspects, the administration of such compositions also reduces pain reliever use and minimizes blood transfusion after surgery. As shown in the examples, the amount of blood transfused in the intervention group was only ⅙ of the fasting group (33±19 ml compared with 186±65 ml, $p<0.05$).

Terminology and Definitions

In describing implementations of preoperative compositions and methods of preparation thereof, the following terminology will be used in accordance with the definitions and explanations set out below. Notwithstanding, other terminology, definitions, and explanations may be found throughout this document, as well. Unless specifically noted, it is intended that the words and phrases in the specification and the claims be given their plain, ordinary, and accustomed meaning to those of ordinary skill in the applicable arts.

The singular forms "a," "an," and "the" include plural referents unless the context clearly dictates otherwise. Thus, for example, reference to "a step" includes reference to one or more of such steps.

The word "exemplary," "example," or various forms thereof are used herein to mean serving as an example, instance, or illustration. Any aspect or implementation described herein as "exemplary" or as an "example" is not necessarily to be construed as preferred or advantageous over other aspects or implementations. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented but have been omitted for purposes of brevity.

As used herein, the term "surgery" refers to a medical procedure performed for the purpose of structurally altering the human body by the incision or destruction of tissues where general anesthesia is required. As used herein, the term encompasses the diagnostic or therapeutic treatment of conditions or disease processes by any instruments causing localized alteration or transposition of live human tissue which include lasers, ultrasound, ionizing radiation, scalpels, probes, and needles. The tissue can be cut, burned, vaporized, frozen, sutured, probed, or manipulated by closed reductions for major dislocations or fractures, or otherwise altered by mechanical, thermal, light-based, electromagnetic, or chemical means. As referenced herein, the start of surgery is when the patient is given general anesthesia.

As used herein, the term "isolate milk protein" refers to a protein powder produced from milk, preferably from a ruminant animal, for example, a cow or a goat, which includes whey and casein. Accordingly, the isolate milk protein includes all nine essential amino acids. In some aspects, the isolate milk protein is free of lactose. In other aspects, the isolate milk protein includes at least one ingredient selected from whole milk powder, demineralized whey powder 40% (also referred to herein as "whey demin 40"), isolate whey and protein.

As used herein, the term "isolate pea protein" refers to protein isolated from peas, preferably the yellow pea. The isolate pea protein includes all nine essential amino acids and is a great source of branched-chain amino acids.

As used herein, the term "surgical stress" refers to a systemic response to surgical injury. It is characterized by activation of the sympathetic nervous system, endocrine responses, and immunological and histological changes, for example, perturbations in the inflammatory, acute, phase, hormonal, and genomic responses. In some circumstances, metabolism is impacted, and thus optimal nutrition support is often required to ensure positive patient outcomes following forgery. In some aspects, oxidative stress is also an indicator of surgical stress.

The Nutritional Composition

Some studies show that supplementation with branched-chain amino acids can reduce muscle mass loss, muscle contraction loss, and postoperative acute inflammatory response. Studies have also shown that the administration of probiotics one day before and for fifteen days after surgery helps reduce the incidence of complications after surgery, especially preventing severe infections. Additionally, low preoperative blood selenium level is also a risk factor for postoperative mortality. Reduced selenium concentration in the blood has been shown to be correlated to multiple organ failure. In fact, survivors of surgery have higher blood selenium levels than patients who died during surgery. Selenium acts as a co-enzyme in the endogenous defense system that protects cells from oxidative stress. A study found that four weeks of supplementing with 200 μg selenium before heart surgery improved insulin resistance. One preoperative nutrition guideline recommended providing 150-210 μg selenium dose to protect cells from oxidative stress. Vitamin K2 is not only a vitamin but a hormone that helps increase the toughness of the vessel wall and tissue integrity. A dose of 360 μg of vitamin K2 for 14 weeks was shown to increase arterial wall strength, improve renal tissue, and increase bone mass and was found not to be toxic. Thus, the nutritional composition described herein provides these needed nutrients for improved recovery from surgical stress. Accordingly, the nutritional composition includes branched-chain amino acids, selenium, and vitamin K2.

Both isolate milk protein and isolate pea protein contains high levels of branch chain amino acids. In a particular implementation, the nutritional composition includes soy milk, isolate milk protein, isolate pea protein, a composition of probiotic organisms, and a composition of vitamins and minerals comprising at least selenium and vitamin K12. In liquid form, the soy milk is prepared from 100 g of soybeans in 1000 ml water. In some aspects, one weight percent of the soy milk is protein. In the powder form, instant soy milk powder contains 37% protein. In some implementations, the isolate milk protein is at least partially produced by whole milk powder, preferably unsweetened whole milk powder. In some implementations, the nutritional composition includes between 3-5 g branched chain amino acids, for example, provided from 4-8 g (e.g., 5.8 g) isolate pea protein, the soy milk, and between 6-10 g isolate milk protein (which also originates from the unsweetened whole milk powder). In some aspects, the nutritional composition includes at least 3.3% (w/v) by weight isolate milk protein and at least 2.4% (w/v) by weight isolate pea protein.

The composition of probiotic organisms includes at least one species of bacteria selected from the group consisting of *Lactobacillus acidophilus, Lactobacillus reuteri, Lactobacillus casei, Bifidobacterium longum*, and *Streptococcus faecalis*. In some aspects, the composition of probiotic organisms is microencapsulated. In certain implementations, the composition of probiotic organisms includes $3\times10^8$ colony-forming units of each species of bacteria.

The composition of vitamins and minerals includes between 300-500 μg vitamin K2 and between 150 and 300 μg selenium. In some implementations, the composition of vitamins and minerals further includes at least vitamin or mineral selected from the group consisting of: retinol, carotene, vitamin E, vitamin D, vitamin K1, a vitamin B, vitamin C, iron, magnesium, and zinc. In certain implementations, vitamin D is vitamin D3. In some aspects, vitamin B includes thiamin, riboflavin, niacin, vitamin B6, vitamin B7, vitamin B9, vitamin B12, or a combination thereof. In particular implementations, the composition of vitamins and minerals includes 850-900 μg retinol, 4-7 mg carotene, 10-20 mg vitamin E, 10-20 mg vitamin D, 70-90 μg vitamin K1, 0.5-1.5 mg thiamin, 0.5-1.5 mg riboflavin, 10-20 mg niacin, 0.5-2.0 mg vitamin B6, 20-30 μg vitamin B7, 350-450 μg vitamin B9, 1.5-4.0 μg vitamin B12, 70-80 mg vitamin C, 5-10 mg iron, 300-350 mg magnesium, and/or 20-30 μg zinc.

In certain implementations, the nutritional composition also includes medium chain triglyceride. For example, the nutritional composition includes 2-3% (w/v) by weight medium chain triglyceride. In some aspects, the nutritional composition also includes natural and artificial flavors, sweeteners, salt, flavor enhancers, color additives, emulsifiers, stabilizers, fats, and/or preservatives.

In a particular implementation, the nutritional composition in a liquid form comprises:

between 70-75% (e.g., 72.2%) by volume soy milk;

between 7-10% (e.g., 8.6%) by weight whole milk powder;

between 2-5% (e.g., 3.3%) by weight isolate milk protein; and between 2-4% (e.g., 2.4%) by weight isolate pea protein.

In a particular implementation, the ingredients of the nutritional composition in a liquid form and their respective amounts are listed in Table 3.

In a particular embodiment, the nutritional composition in a powder form comprises:

between 10.7-14.7% (e.g., 12.4%) by weight instant soy milk powder;

between 16.3-22.4% (e.g., 18.9%) by weight whole milk powder;

between 9.3-12.8% (e.g., 10.8%) by weight isolate milk protein; and between 6.7-9.2% (e.g., 7.8%) by weight isolate pea protein.

In a particular embodiment, the ingredients of the nutritional composition in a powder form and their respective amounts are listed in Table 8.

In some aspects, the nutritional composition is a 300 ml solution comprising between 15-20 g protein, of which at least 20% are branched-chain amino acids. For example, the nutritional the nutritional composition is a 300 ml solution containing 18 g protein, where 20.7% of the protein are branched-chain amino acids. The protein distribution of the nutritional composition is high in cysteine, which acts as an endogenous antioxidant.

In some implementations, the nutritional composition provides between 350-400 Kcal, between 15-20 g protein (of which at least 20% are branched-chain amino acids), 35-40 g carbohydrate, and 20-25 g fat. In particular implementations, the nutritional composition provides 390 Kcal in the form of 18 g protein, 39 g carbohydrate, and 21.6 g fat. In some implementations, the nutritional composition provides between 8.1 to 15.7 Kcal/kg body weight of the patient, 0.06-0.1 g branched-chain amino acid/kg body weight of the patient, 5-9.8 μg vitamin K2/kg body weight of the patient, and 2.8-5.4 μg selenium/kg body weight of the patient. Table 1 lists the nutritional information for certain implementations of the nutritional composition.

TABLE 1

| Nutrients | Units | From 300 ml nutritional composition | Dietary Reference Intakes | per kg body weight from both preoperative compositions |
|---|---|---|---|---|
| Energy | Kcal | 390.0 | 35 Kcal/kg | 11.9 ± 3.8 |
| Protein | g | 18.0 | 1.5 g/kg | 0.4 ± 0.1 |
| Branched-chain amino acids | g | 3.7 | | 0.08 ± 0.02 |
| Isolate milk protein | g | 8.7 | | 0.2 ± 0.06 |
| Isolate pea protein | g | 5.8 | | 0.1 ± 0.04 |
| Carbohydrate | g | 39.0 | 130 | 1.8 ± 0.6 |
| Fiber | g | 5.7 | 19-27 | 0.1 ± 0.04 |
| Lactose | g | 16.4 | 20 | 0.3 ± 0.1 |
| Glucose | g | 7.7 | | 0.2 ± 0.1 |
| Fat | g | 21.6 | 70-80 | 0.4 ± 0.1 |
| Trans Fat | g | 0.0 | 0.0 | 0 ± 0 |
| Mono-Unsaturated Fatty Acid | g | 1.7 | 29-34 | 0.03 ± 0.01 |

TABLE 1-continued

| Nutrients | Units | From 300 ml nutritional composition | Dietary Reference Intakes | per kg body weight from both preoperative compositions |
|---|---|---|---|---|
| Poly Unsaturated Fatty Acid | g | 1.7 | 16-21 | 0.03 ± 0.01 |
| Saturated Fatty Acid | g | 9.4 | 20-30 | 0.2 ± 0.1 |
| Omega-3 | g | 0.1 | 2.2 | 0.002 ± 0.001 |
| Omega-6 | g | 2.1 | 14-18 | 0.043 ± 0.014 |
| Cholesterol | mg | 30.3 | <600 | 0.6 ± 0.2 |
| MCT | g | 6.3 | 52-103 | 0.1 ± 0.04 |
| Vitamins | | | | |
| Vitamin A-Retinol | μg | 900.0 | 900-3000 | 18.4 ± 5.9 |
| Carotene | mg | 6.0 | 6-15 | 0.1 ± 0.04 |
| Vitamin E-Tocopherol | mg | 15.0 | 15-22 | 0.3 ± 0.1 |
| Vitamin D3-Calciferol | μg | 15.0 | 15-20 | 0.3 ± 0.1 |
| Vitamin K1 | μg | 75.0 | 75-120 | 1.5 ± 0.5 |
| Vitamin K2** | μg | 360.0 | 360 | 7.4 ± 2.4 |
| Vitamin B1-Thiamine | mg | 0.9 | 0.9-1.2 | 0.02 ± 0.01 |
| Vitamin B2-Riboflavin | mg | 0.9 | 0.9-1.3 | 0.02 ± 0.01 |
| Vitamin PP-B3-Niacin | mg | 14.0 | 14-16 | 0.3 ± 0.1 |
| Vitamin B5-Pantothenic acid | mg | 18.5 | 5 | 0.4 ± 0.1 |
| Vitamin B6-Pyridoxine | mg | 1.3 | 1.3-1.7 | 0 ± 0 |
| Vitamin B7-B8-Vitamin H | μg | 25.0 | 25-30 | 0.5 ± 0.2 |
| Vitamin B9-Folate | μg | 400.0 | 400 | 8.2 ± 2.6 |
| Vitamin B12-Cyanocobalamine | μg | 2.4 | 2.4 | 0.05 ± 0.02 |
| Vitamin C-Ascorbic | mg | 75.0 | 75-90 | 1.5 ± 0.5 |
| Minerals and Trace Elements | | | | |
| Calcium | mg | 393.0 | 1000-1300 | 8 ± 2.6 |
| Phosphorus | mg | 462.0 | 700-1250 | 9.5 ± 3 |
| Iron | mg | 8.0 | 8-18 | 0.2 ± 0.1 |
| Sodium | mg | 177.0 | 1200-1500 | 3.6 ± 1.2 |
| Potassium | mg | 768.0 | 2000-4700 | 15.7 ± 5.1 |
| Magnesium | mg | 320.0 | 320-420 | 6.5 ± 2.1 |
| Zinc | mg | 25.0 | 25 | 0.5 ± 0.2 |
| Manganese | mg | 0.6 | 1.8-2.3 | 0.01 ± 0.004 |
| Copper | μg | 261.0 | 900 | 5.3 ± 1.7 |
| Fluoride | μg | 0.0 | 3000-4000 | 0 ± 0 |
| Iodine | μg | 6.7 | 150 | 0.1 ± 0.04 |
| Selenium | μg | 200.0 | 500 | 4.1 ± 1.3 |

The Sugar Solution

Between about 2.3 and about 6.5 hours prior to surgery, the patient is orally administered 200 ml of the sugar solution. In some aspects, the amount sugar provided to the patient via the sugar solution is about 0.7 to about 1.3 g sugar/kg body weight of the patient, for example, around 0.7 g/kg body weight, around 0.8 g/kg body weight, around 0.9 g/kg body weight, around 1.0 g/kg body weight, around 1.1 g/kg body weight, around 1.2 g/kg body weight, or around 1.3 g/kg body weight. In a particular implementation, the sugar solution includes 25% sugar in a water-based composition. The sugars provide maltodextrin. Table 2 lists the nutritional information for certain implementations of the sugar solution.

TABLE 2

| Nutrients | Units | From 200 ml Sugar Solution | Dietary Reference Intake | Nutrients intake per kg body weight from both preoperative compositions |
|---|---|---|---|---|
| Energy | Kcal | 190 | 35 Kcal/kg | 11.9 ± 3.8 |
| Carbohydrate | g | 50 | 130 | 1.8 ± 0.6 |
| Maltodextrin | g | 50 | | 1.0 ± 0.3 |

The preoperative compositions of the present disclosure help reduce postoperative complications and the need for pain relievers. They also minimize blood transfusions needed during and after surgery. Therefore, the preoperative compositions improve the quality and outcomes of surgical procedures by helping patients reduce treatment costs and recover more quickly. They also allow surgeons and medical staff to use resources more effectively thereby providing additional labor resources to society.

EXAMPLES

The present disclosure is further illustrated by the following examples that should not be construed as limiting. The contents of all references, patents, and published patent applications cited throughout this application, as well as the Figures, are incorporated herein by reference in their entirety for all purposes.

1. Method of Producing an Exemplary Nutritional Composition in a Liquid Form

Table 3 lists the weight or volume percent distribution of the ingredients in an exemplary nutritional composition in a liquid form. Table 4 lists the ingredients by group for the production process. Table 5 lists the nutritional information for the exemplary nutritional composition in a liquid form.

TABLE 3

| Ingredient | Percentage by Weight/ Volume (w/v) or Volume/ Volume (v/v) |
|---|---|
| Soy milk 1% protein (1000 ml of soy milk made from 100 g soybeans) | 72.2% (ml/100 ml) |
| Unsweetened whole milk powder (24% protein) | 8.6% (g/100 ml) |
| Milk Protein Isolate (88% protein) | 3.3% (g/100 ml) |
| Pea Protein Isolate (80% protein) | 2.4% (g/100 ml) |
| Distilled water | 9.2% (ml/100 ml) |
| Microencapsulation probiotics and other supplements: Whey Demin 40; Nondairy-cream (Nondairy-cream); MCT (Medium-chain triglyceride); Fructose Oligosaccharide; Salt; PALSGAARD ®RecMilk (emulsifier and stabilizer); Elemental iron (iron III hydroxide); Magnesium; Elemental zinc (zinc gluconate); Selenium; vitamin A (Retinyl acetate); Carotene; vitamin E (DL-α Tocopherol acetate); vitamin D3; vitamin K1; vitamin K2; vitamin B1-Thiamine; vitamin B2-Riboflavin; Vitamin PP-B3-Niacin; vitamin C-Ascorbic; vitamin B6; vitamin B7; vitamin B9 (folic acid); vitamin C. | 13.5% (g/100 ml) |

TABLE 4

| Group | Ingredients | Quantity |
|---|---|---|
| 1 | Soy milk (1.1% protein) | 72.2% (ml/100 ml) |
| 2 | Unsweetened whole milk powder (24% protein) | 8.6% (g/100 ml) |
| 3 | Milk Protein Isolate (88% protein) | 3.3% (g/100 ml) |
| 4 | Pea Protein Isolate (80% protein) | 2.4% (g/100 ml) |
| 5 | Distilled water | 9.2% (ml/100 ml) |
| 6 | Microencapsulated probiotics (in a simple microencapsulation sack) | |
| | *Lactobacillus acidophilus* | $3 \times 10^8$ CFUs/300 ml |
| | *Lactobacillus reuteri* | $3 \times 10^8$ CFUs/300 ml |

TABLE 4-continued

| Group | Ingredients | Quantity |
|---|---|---|
| | *Lactobacillus casei* | 3 × $10^8$ CFUs/300 ml |
| | *Bifidobacterium longum* | 3 × $10^8$ CFUs/300 ml |
| | *Streptococcus faecalis* | 3 × $10^8$ CFUs/300 ml |
| 7 | Supplements | |
| | Whey demin 40 | 2.5% (g/100 ml) |
| | Nondairy cream | 3.5% (g/100 ml) |
| | MCT (Medium chain triglyceride) | 2.5% (g/100 ml) |
| | Fructose Oligo Saccharide | 3.5% (g/100 ml) |
| | Salt | 0.01% (g/100 ml) |
| | PALSGAARD ®RecMilk (emulsifier and stabilizer) | 0.2% (g/100 ml) |
| | Retinol | 3000 μg/1000 ml |
| | Carotene | 20 mg/1000 ml |
| | Vitamin E-Tocopherol | 48 mg/1000 ml |
| | Vitamin D3 | 50 μg/1000 ml |
| | Vitamin K1 | 224 μg/1000 ml |
| | Vitamin K2 | 1200 μg/1000 ml |
| | Vitamin B1-Thiamine | 3 mg/1000 ml |
| | Vitamin B2-Riboflavin | 3 mg/1000 ml |
| | Vitamin PP-B3-Niacin | 41 mg/1000 ml |
| | Vitamin B6 | 4 mg/1000 ml |
| | Vitamin B7 | 83 μg/1000 ml |
| | Vitamin B9 | 1333 μg/1000 ml |
| | Vitamin B12 | 5 μg/1000 ml |
| | Vitamin C-Ascorbic | 250 mg/1000 ml |
| | Iron | 21 mg/1000 ml |
| | Magnesium | 819 mg/1000 ml |
| | Zinc | 77 mg/1000 ml |
| | Selenium | 667 μg/1000 ml |

TABLE 5

| Nutrients | Unit | Content/100 ml | Content/300 ml |
|---|---|---|---|
| Main nutritional ingredients | | | |
| Energy | kcal | 130.0 | 390.0 |
| Protein | g | 6.0 | 18.0 |
| Branched Chain Amino Acid | % | 20.7 | 20.7 |
| Carbohydrate | g | 13.0 | 39.0 |
| Fiber | g | 1.9 | 5.7 |
| Lactose | g | 5.5 | 16.4 |
| Glucose | g | 2.6 | 7.7 |
| Fat | g | 7.2 | 21.6 |
| Trans fat | g | 0.0 | 0.0 |
| Monounsaturated Fatty Acid | g | 0.6 | 1.7 |
| Poly Unsaturated Fatty Acid | g | 0.6 | 1.7 |
| Saturate Fatty Acid | g | 3.1 | 9.4 |
| Omega3 | g | 0.0 | 0.1 |
| Omega6 | g | 0.7 | 2.1 |
| Cholesterol | mg | 10.1 | 30.3 |
| MCT | g | 2.1 | 6.3 |
| Vitamins | | | |
| Retinol | μg | 300.0 | 900.0 |
| Carotene | mg | 2.0 | 6.0 |
| Vitamin E-Tocopherol | mg | 5.0 | 15.0 |
| Vitamin D3 | μg | 5.0 | 15.0 |
| Vitamin K1 | μg | 25.0 | 75.0 |
| Vitamin K2 | μg | 120.0 | 360.0 |
| Vitamin B1-Thiamine | mg | 0.3 | 0.9 |
| Vitamin B2-Riboflavin | mg | 0.3 | 0.9 |
| Vitamin PP-B3-Niacin | mg | 4.7 | 14.0 |
| Vitamin B5 | mg | 6.2 | 18.5 |
| Vitamin B6 | mg | 0.4 | 1.3 |
| Vitamin B7 | μg | 8.3 | 25.0 |
| Vitamin B9 | μg | 133.3 | 400.0 |
| Vitamin B12 | μg | 0.8 | 2.4 |
| Vitamin C-Ascorbic | mg | 25.0 | 75.0 |
| Minerals and trace elements | | | |
| Calcium | mg | 131.0 | 393.0 |
| Phosphorus | mg | 154.0 | 462.0 |
| Iron | mg | 2.7 | 8.0 |
| Sodium | mg | 59.0 | 177.0 |

TABLE 5-continued

| Nutrients | Unit | Content/100 ml | Content/300 ml |
|---|---|---|---|
| Potassium | mg | 256.0 | 768.0 |
| Magnesium | mg | 106.7 | 320.0 |
| Zinc | mg | 8.3 | 25.0 |
| Manganese | mg | 0.2 | 0.6 |
| Copper | μg | 87.0 | 261.0 |
| Fluoride | μg | 0.0 | 0.0 |
| Iodine | μg | 2.2 | 6.7 |
| Selenium | μg | 66.7 | 200.0 |
| Amino Acid Score* | | 978.9 | 978.9 |
| Inflammatory Index Score** | | 107.5 | 322.4 |

Figure 2:
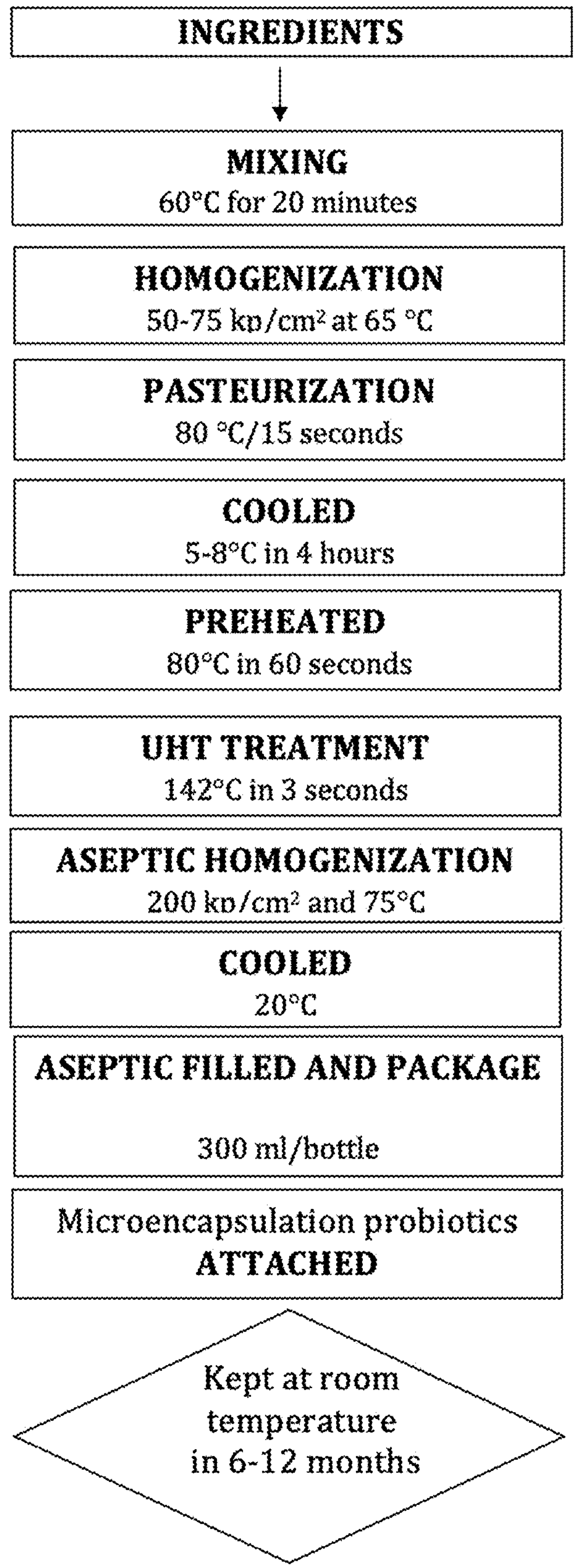
FIG. 2 depicts, in accordance with certain implementations, a schematic for the production of the nutritional composition in a liquid form disclosed herein.

*WHO 2007. Protein and Amino Acid Requirements in Human Nutrition Report of a Joint WHO/FAO/UNU Expert Consultation. WHO, 935, 2007.
**Cavicchia et al. "A new dietary inflammatory index predicts interval changes in serum high-sensitivity C-reactive protein." *J Nutr.* 2009; 139(12): 2365-2372.
≥200 Strong anti-inflammatory
101-200 Moderate anti-inflammatory
1-100 Mild anti-inflammatory
−1 to −100 Causes mild inflammation
−101 to −200 Moderate inflammation
≤−201 Causes strong inflammation FIG. 2 is a schematic of the process of producing a liquid nutritional composition described herein. The production process begins with heating water and soy milk 1% protein to a 50° C. temperature. Then the mixture of water and soy milk is mixed with unsweetened whole milk powder, whey demin 40, isolate whey protein, isolate pea protein, MCT, soluble fiber, and emulsifier by a mixing bath with a paddle stir. These ingredients are then heated at 60° C. for 20 minutes until the suspension is completely dissolved. The remaining nutrients are then added to the suspension, which is homogenized at 50-75 kp/$cm^2$ and 65° C.

The mixture is sterilized at 80° C. for 15 seconds by a thin panel or telescopic heat exchanger. Next, the suspension is cooled by a tube-type heat exchanger and held at 5-8° C. for 4 hours. The suspension is preheated at 80° C. for 60 seconds before undergoing ultra-high-temperature (UHT) process (142° C. for 3 seconds). The UHT-processed suspension is homogenized again in the aseptic condition at 200 kp/$cm^2$ and 75° C. The product is preserved by pouring into pasteurized packaging, 300 ml per unit, after cooled down to 20° C.

The final product may be kept at room temperature for at least six (6) months, though preferably less than 12 months. A composition of microencapsulated probiotics is attached to the product or designed to be contained in the lid of a milk carton. The composition microencapsulation probiotics includes *L. Acidophilus* 3×$10^8$ CFU, *L. Reuteri* 3×$10^8$ CFU, *L. Casei* 3×$10^8$ CFU, *B. Longum* 3×$10^8$ CFU, and *S. Faecalis* 3×$10^8$ CFU.

2. Method of Producing an Exemplary Sugar Solution in a Liquid Form

Table 6 lists the weight or volume percent distribution of the ingredients in an exemplary sugar solution in a liquid form. Table 7 lists the nutritional information for the exemplary nutritional composition in a liquid form.

TABLE 6

| Group | Ingredients | Quantity |
|---|---|---|
| 1 | Maltodextrin (type 10 Glucose molecules) 25% | 25% (25 g/100 ml) |
| 2 | Distilled water | 75% (75 ml/100 ml) |

TABLE 7

| Nutrients | Unit | Content/100 ml | Content/200 ml |
|---|---|---|---|
| Energy | kcal | 95.0 | 190.0 |
| Carbohydrate | g | 25.0 | 50.0 |

Figure 3:
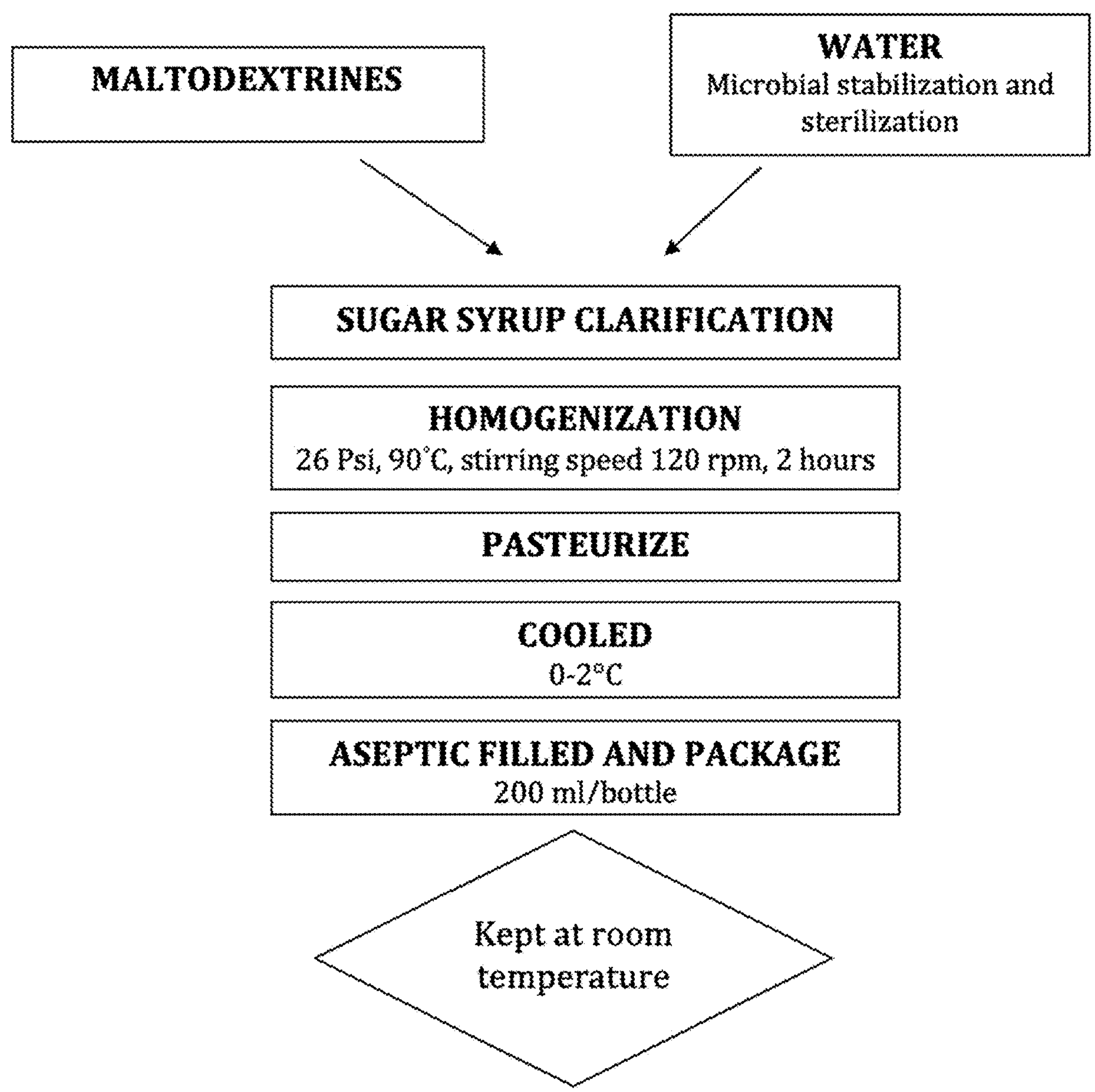
FIG. 3 depicts, in accordance with certain implementations, a schematic for the production of the sugar solution disclosed herein.

FIG. 3 is a schematic of the process of producing a sugar solution described herein. The process begins with pouring water into a cooking basin with an electric motor paddle and then adding maltodextrin to the bath so that the water content is five times the total sugar mass. The heated steam pressure was adjusted to 26 Psi within the cooking basin. The water and maltodextrin mixture is cooked with stirring (120 rpm.) for about 2 hours until the solution reaches 90° C.—when bubbles appear, and the mixture appears homogeneous.

The resulting syrup is removed from the cooking pot and filtered to remove impurities. The filtered syrup is them transferred to the 1500 liters tanks and cooled to 0-2° C. (for example, by the heat transfer pipes arranged in the tank's spiral). The cooled syrup is then pumped to the tank and transferred to the can extractor's extraction tank. The filling unit consists of 24 taps fitted with a valve system that automatically locks and opens, controlled by the POC programming system. Finished products are poured at the same time into 24 cans with a volume of 200 ml each.

Each can is then conveyed to the lid draw frame machine. All conveyors are controlled by a geared motor using 220 V power, capacity 0.5 Kw/h. After the lid is grafted, the conveyor belt will transfer the finished can to a water tank with four resistive bars to cool it up to a temperature of about 30° C. and moved to the shrink film packaging area and labeled.

3. Method of Producing an Exemplary Nutritional Composition in a Powder Form

Table 8 lists the weight percent distribution of the ingredients in an exemplary nutritional composition in a powder form. Table 9 lists the ingredients by group for the production process. Table 10 lists the nutritional information for the exemplary nutritional composition in a powder form.

TABLE 8

| Ingredient | Percentage by Weight/ Weight (w/w) |
|---|---|
| Instant soy milk powder (37% Protein) | 12.4 (g/100 g) |
| Unsweetened whole milk powder (24% protein) | 18.9 (g/100 g) |
| Milk Protein Isolate (88% protein) | 10.8 (g/100 g) |
| Pea Protein Isolate (80% protein) | 7.8 (g/100 g) |
| Microencapsulation probiotics and other supplements: Whey Demin 40; Nondairy-cream (Nondairy-cream); MCT (Medium-chain Triglyceride); Fructose Oligosaccharide; Salt; PALSGAARD ®RecMilk (emulsifier and stabilizer); elemental iron (iron III hydroxide); Magnesium; elemental zinc (zinc gluconate); Selenium; vitamin A (Retinyl acetate); Carotene; vitamin E (DL-α Tocopherol acetate); vitamin D3; vitamin K1; vitamin K2; vitamin B1-Thiamine; vitamin B2-Riboflavin; vitamin PP-B3-Niacin; vitamin B6; vitamin B7; vitamin B9 (folic acid); vitamin C-Ascorbic. | 50.1 (g/100 g) |

TABLE 9

| Group | Ingredients | Quantity |
|---|---|---|
| 1 | Instant soy milk powder (37% Protein) | 12.4% (g/100 g) |
| 2 | Unsweetened whole milk powder (24% protein) | 18.9% (g/100 g) |
| 3 | Milk Protein Isolate (88% protein) | 10.8% (g/100 g) |
| 4 | Pea Protein Isolate (80% protein) | 7.8% (g/100 g) |
| 5 | Microencapsulation probiotics (microencapsulation probiotics) | |
| | *Lactobacillus acidophilus* | 3.3 × 10^8 CFUs/100 g |
| | *Lactobacillus reuteri* | 3.3 × 10^8 CFUs/100 g |
| | *Lactobacillus casei* | 3.3 × 10^8 CFUs/100 g |
| | *Bifidobacterium longum* | 3.3 × 10^8 CFUs/100 g |
| | *Streptococcus faecalis* | 3.3 × 10^8 CFUs/100 g |
| 6 | Supplements | |
| | Whey demin 40 | 8.2% (g/100 g) |
| | Nondairy-cream | 11.4% (g/100 g) |
| | MCT (Medium chain tryglyceride) | 8.2% (g/100 g) |
| | Fructose Oligo Saccharide | 11.4% (g/100 g) |
| | Salt | 0.03% (g/100 g) |
| | PALSGAARD ® RecMilk (emulsifier and stabilizer) | 0.7% (g/100 g) |
| | Retinol | 979.1 μg/100 g |
| | Carotene | 6.5 mg/100 g |
| | Vitamin E-Tocopherol | 15.7 mg/100 g |
| | Vitamin D3 | 16.3 μg/100 g |
| | Vitamin K1 | 73.1 μg/100 g |
| | Vitamin K2 | 391.7 μg/100 g |
| | Vitamin B1-Thiamine | 1.0 mg/100 g |
| | Vitamin B2-Riboflavin | 1.0 mg/100 g |
| | Vitamin PP-B3-Niacin | 13.4 mg/100 g |
| | Vitamin B6 | 1.3 mg/100 g |
| | Vitamin B7 | 27.1 μg/100 g |
| | Vitamin B9 | 435.1 μg/100 g |
| | Vitamin B12 | 1.6 μg/100 g |
| | Vitamin C-Ascorbic | 81.6 mg/100 g |
| | Iron | 6.9 mg/100 g |
| | Magnesium | 267.3 mg/100 g |
| | Zinc | 25.1 mg/100 g |
| | Selenium | 217.7 μg/100 g |

TABLE 10

| Nutrients | Unit | Content/100 g | Content/300 ml |
|---|---|---|---|
| Main nutritional ingredients | | | |
| Energy | kcal | 424.4 | 390.0 |
| Protein | g | 19.6 | 18.0 |
| Branched Chain Amino Acid* | % | 20.7 | 20.7 |
| Amino Acid Score* | | 978.9 | 978.9 |
| Carbohydrate | g | 42.4 | 39.0 |
| Fiber | g | 6.2 | 5.7 |
| Lactose | g | 17.8 | 16.4 |
| Glucose | g | 8.4 | 7.7 |
| Fat | g | 23.5 | 21.6 |
| Trans Fat | g | 0.0 | 0.0 |
| Mono-Unsaturated Fatty Acid | g | 1.8 | 1.7 |
| Poly Unsaturated Fatty Acid | g | 1.8 | 1.7 |
| Saturate Fatty Acid | g | 10.2 | 9.4 |
| Omega-3 | g | 0.1 | 0.1 |
| Omega-6 | g | 2.3 | 2.1 |
| Cholesterol | mg | 33.0 | 30.3 |
| MCT | g | 6.9 | 6.3 |
| Vitamins | | | |
| Vitamin A-Retinol | μg | 979.3 | 900.0 |
| Carotene | mg | 6.5 | 6.0 |
| Vitamin E-Tocopherol | mg | 16.3 | 15.0 |
| Vitamin D3-Calciferol | μg | 16.3 | 15.0 |
| Vitamin K1 | μg | 81.6 | 75.0 |
| Vitamin K2 | μg | 391.7 | 360.0 |
| Vitamin B1-Thiamine | mg | 1.0 | 0.9 |
| Vitamin B2-Riboflavin | mg | 1.0 | 0.9 |
| Vitamin PP-B3-Niacin | mg | 15.2 | 14.0 |
| Vitamin B5-Pantothenic acid | mg | 20.1 | 18.5 |
| Vitamin B6-Pyridoxine | mg | 1.4 | 1.3 |

TABLE 10-continued

| Nutrients | Unit | Content/100 g | Content/300 ml |
|---|---|---|---|
| Vitamin B7-B8-Vitamin H | μg | 27.2 | 25.0 |
| Vitamin B9-Folate | μg | 435.3 | 400.0 |
| Vitamin B12-Cyanocobalamine | μg | 2.6 | 2.4 |
| Vitamin C-Ascorbic | mg | 81.6 | 75.0 |
| Minerals and trace elements | | | |
| Calcium | mg | 427.6 | 393.0 |
| Phosphorus | mg | 502.7 | 462.0 |
| Iron | mg | 8.7 | 8.0 |
| Sodium | mg | 192.6 | 177.0 |
| Potassium | mg | 835.7 | 768.0 |
| Magnesium | mg | 348.2 | 320.0 |
| Zinc | mg | 27.2 | 25.0 |
| Manganese | mg | 0.7 | 0.6 |
| Copper | μg | 284.0 | 261.0 |
| Fluoride | μg | 0.0 | 0.0 |
| Iodine | μg | 7.3 | 6.7 |
| Selenium | μg | 217.6 | 200.0 |
| Inflammatory Index Score** | | 350.8 | 322.4 |

*WHO 2007. Protein and Amino Acid Requirements in Human Nutrition Report of a Joint WHO/FAO/UNU Expert Consultation. WHO, 935, 2007.
Good protein source if Branch Chain Amino Acid >20%, Amino Acid Score >100

**Cavicchia et al. "A new dietary inflammatory index predicts interval changes in serum high-sensitivity C-reactive protein." *J Nutr.* 2009; 139(12): 2365-2372.

Figure 4:
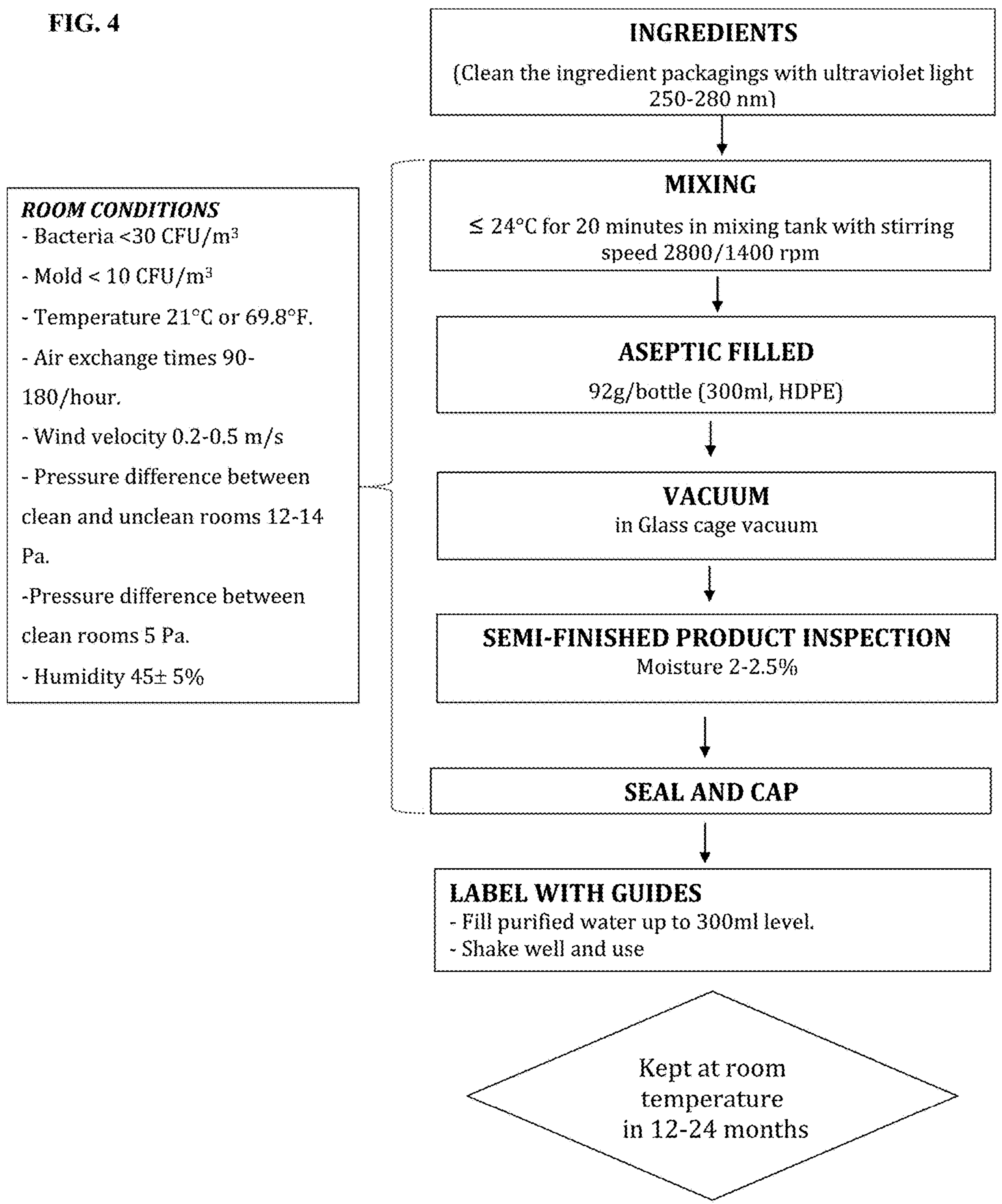
FIG. 4 depicts, in accordance with certain implementations, a schematic for the production of the nutritional composition in a powder form disclosed herein.

⩾200 Strong anti-inflammatory
101-200 Moderate anti-inflammatory
1-100 Mild anti-inflammatory
−1 to −100 Causes mild inflammation
−101 to −200 Moderate inflammation
⩽−201 Causes strong inflammation FIG. 4 is a schematic of the process of producing a powder nutritional composition described herein. The production process begins with instant soy milk powder, unsweetened whole milk powder, whey demin 40, isolate whey protein, isolate pea protein, MCT, soluble fiber, probiotics and emulsifier in a mixing bath with a paddle stirring at 24° C. for 20 minutes. The product is preserved by filling into 300 ml pasteurized packaging, 92 g per unit. Before sealing, the milk bottle is vacuum sealed to ensure moisture is 2-2.5%.

The final product is labeled with a guide for pouring purified water up to 300 ml level, shaking well and using. The dry product may be kept at room temperature for at least 12 months, though preferably less than 24 months.

4. Method of Producing an Exemplary Sugar Solution in a Powder Form

Table 11 lists the weight of the ingredients in an exemplary sugar solution in a powder form in one unit (e.g., a bottle). Table 12 lists the nutritional information for the exemplary nutritional composition in a powder form.

TABLE 11

| Group | Ingredients | Quantity |
|---|---|---|
| 1 | Maltodextrin (type 10 Glucose molecules) 100% | 50 g/bottle |

TABLE 12

| Nutrients | Unit | Content/bottle |
|---|---|---|
| Energy | kcal | 190.0 |
| Carbohydrate | g | 50.0 |

Figure 5:
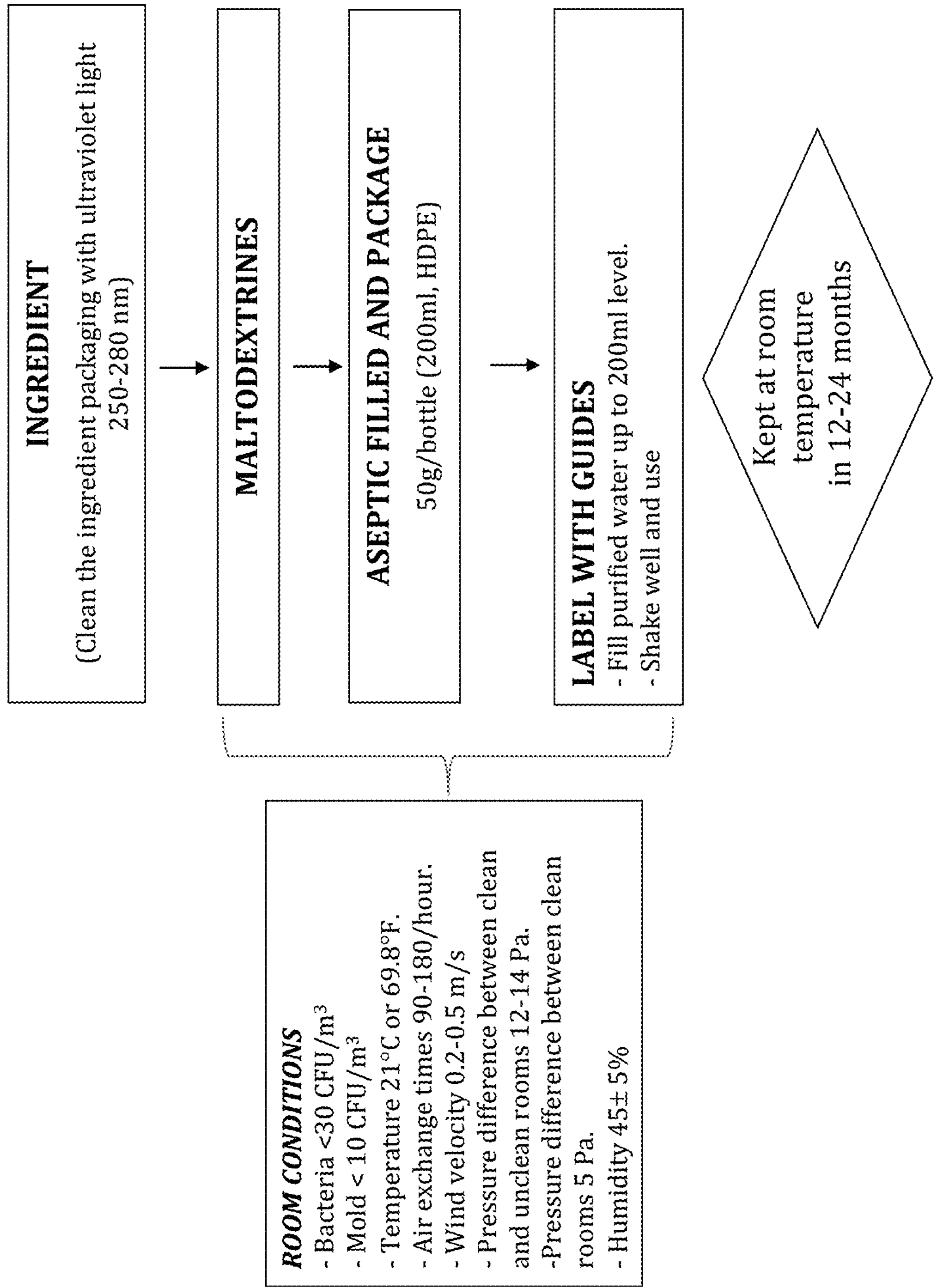
FIG. 5 depicts, in accordance with certain implementations, a schematic for the production of a sugar powder unit disclosed herein.

FIG. 5 is a schematic of the process of producing a sugar powder unit described herein. The product is preserved by filling into 200 ml pasteurized packaging, 50 g per unit. The final product is labeled with a guide for pouring purified water up to a 200 ml level, shaking well and using. The sugar powder unit may be kept at room temperature for at least 12 months, though preferably less than 24 months.

5. Study of Impact on Metabolic Surgical Trauma, Hormonal Responses, Postoperative Complications, and Insulin Resistance A randomized controlled clinical trial was conducted to evaluate whether drinking the described nutritional composition the night before surgery and the described sugar solution at 6:00 AM on the operation day could reduce metabolic surgical trauma, hormonal responses, postoperative complications, and insulin resistance.

144 ASA I-IV orthopedic patients were randomized into four groups, 36 patients in each group. Group 1 patients fasted prior to their surgery. Group 2 patients drank only a placebo composition (aspartame 0.035%, 400 mL) the night before their surgery and another dose of the placebo composition (aspartame 0.035%, 200 mL) at 6:00 AM on their operation day. Group 3 patients were part of the "carbohydrate loading" and drank 400 ml of a composition comprising Maltodextrin 25% the night before their surgery followed by 200 ml of the same composition at 6:00 AM on their operation day. Group 4 patients (named ONS) drank 300 ml of the nutritional composition the night before the surgery followed by 200 ml of the sugar solution.

Blood sample was collected immediately before the anesthesia induction, two hours after the stitched incision, and the fourth day after surgery. The samples were measured for blood glucose, plasma insulin, albumin, cholesterol, and CRP levels and lymphocyte count.

The patient's nutrition status was assessed on the day before operation and the 4th day after surgery. CCI, POMS, Epinephrine dose, and blood transfusion volume were collected. Nutritional status is estimated by NRS (Nutrition Risk Screening); the muscle mass of mid-upper arm (cm); Phage angle)(°); Extracellular Water/Total Body Water; Conut Score (Controlling Nutritional) which calculated from serum albumin (g/dl), lymphocytes/ml and cholesterol (mg/dl).

Gastric volume was assessed by ultrasound (a German LogiQe machine, at a frequency of 3.5 Mhz) before the induction of anesthesia.

The severity of disease requiring orthopedic surgery was assessed by AIS (Abbreviated Injury Scale). The physical status before surgery was measured by ASA. The risk of death from surgery is evaluated by a Preoperative Score to Predict Postoperative Mortality (POSPOM) and Prognostic Nutritional Index (PNI).

Pre-anesthesia thirst was assessed by a Likert scale.

Insulin resistance was determined by the Homeostasis Model Assessment (Homa-IR).

Postoperative complications were estimated by CCI (Comprehensive Complication Index), POMS (Postoperative morbidity survey), Epinephrine dose (mg), blood transfusion (ml), change of CRP (mg/l).

Results

Table 13 shows the status of the patients at the beginning of the study. Table 14 lists the patient's status at the end of the study. Group 1 were the fasting group. Group 2 were the placebo group. Group 3 were the CH loading group. Group 4 were the ONS loading group.

In the beginning, most of the four groups' parameters were the same except for the severity of orthopedic surgery and the nutritional status. These placebo group parameters were lower than that of the fasting and ONS loading group (Table 13).

TABLE 13

| Variables | Group 1 N = 36 | Group 2 N = 36 | Group 3 N = 36 | Group 4 N = 36 |
|---|---|---|---|---|
| Age (years) | 58.8 ± 2.9 | 57.6 ± 2.9 | 57.2 ± 3.4 | 61.9 ± 3.3 |
| Disease status | | | | |
| Abbreviated Injury Scale | 2.7 ± 0.1$^{a}$ | 3.0 ± 0.1$^{b}$ | 2.9 ± 0.1$^{ab}$ | 2.7 ± 0.1$^{a}$ |
| Preoperative status | | | | |
| POSPOM[1] | 11.0 ± 0.5 | 11.6 ± 0.4 | 11.5 ± 0.6 | 12.1 ± 0.6 |
| Likert scale of thirsty* | 2.1 ± 0.2$^{a}$ | 1.8 ± 0.2$^{ab}$ | 1.5 ± 0.1b | 1.5 ± 0.1$^{b}$ |
| Residual gastric volume*(ml) | 25.2 ± 4.6 | 29.4 ± 4.6 | 27.4 ± 4.0 | 20.9 ± 3.9 |
| Homa-IR[2] | 3.7 ± 0.6$^{ab}$ | 2.4 ± 0.3$^{a}$ | 4.3 ± 0.8$^{b}$ | 3.3 ± 0.5$^{ab}$ |
| Prognostic Nutritional Index | 48.6 ± 1.0 | 49.3 ± 1.2 | 48.1 ± 1.2 | 50.6 ± 1.5 |
| CRP (C Reactive Protein) (mg/l) | 14.6 ± 3.8 | 15.7 ± 3.6 | 26.4 ± 7.3 | 23.9 ± 4.6 |
| Mean operative time (hours) | 1.7 ± 0.1 | 1.8 ± 0.1 | 1.7 ± 0.1 | 1.6 ± 0.1 |
| Blood loss (ml) | 234 ± 45 | 269 ± 61 | 205 ± 29 | 195 ± 26 |
| Nutritional status | | | | |
| Nutrition Risk Screening | 2.2 ± 0.3$^{ab}$ | 2.8 ± 0.3$^{a}$ | 2.2 ± 0.3$^{ab}$ | 1.9 ± 0.3$^{b}$ |
| Muscle mass of mid-upper arm (cm) | 18.8 ± 0.4 | 18.5 ± 0.4 | 19.0 ± 0.3 | 19.1 ± 0.5 |
| Muscle strength (kg) | 21.9 ± 1.8 | 21.2 ± 1.9 | 25.1 ± 2.1 | 21.1 ± 1.9 |
| Phage angle (°) | 4.7 ± 0.2 | 4.6 ± 0.2 | 4.9 ± 0.2 | 4.8 ± 0.2 |
| ECW/TBW[3] | 0.40 ± 0.004 | 0.41 ± 0.005 | 0.41 ± 0.005 | 0.40 ± 0.003 |
| Skeletal Muscle Index) (kg/m$^2$ | 7.2 ± 0.9 | 6.6 ± 0.6 | 8.1 ± 0.8 | 6.8 ± 0.6 |
| Conut Score ** | 1.7 ± 0.3 | 1.7 ± 0.3 | 1.9 ± 0.3 | 1.6 ± 0.3 |
| Serum Albumin (g/dl) | 38.2 ± 0.7 | 38.8 ± 0.9 | 37.9 ± 0.6 | 38.7 ± 0.8 |
| Lymphocytes/ml | 2094 ± 107 | 2100 ± 122 | 2036 ± 143 | 2396 ± 222 |
| Cholesterol (mg/dl) | 4.5 ± 0.2 | 4.5 ± 1.2 | 4.2 ± 0.2 | 4.4 ± 0.2 |

Means ± SEM.

[1]Preoperative Score to Predict Postoperative Mortality

[2]Homeostasis Model Assessment

[3]Extracellar Water/Total Body Water

*Before anesthesia

** Calculating from Serum Albumin (g/dl), Lymphocytes/ml and Cholesterol (mg/dl)

Values not sharing a common superscript letter in the same row are significantly different at $p < 0.05$. The difference in these data among four groups was analyzed by the Post hoc test following one-way ANOVA.

TABLE 14

| Variables | Group 1 N = 36 | Group 2 N = 36 | Group 3 N = 36 | Group 4 N = 36 |
|---|---|---|---|---|
| Length of hospital stay (days) | 5.7 ± 0.6 | 5.4 ± 0.3 | 5.7 ± 0.5 | 5.2 ± 0.3 |
| Hospital fee (USD) | 751 ± 57 | 739 ± 57 | 722 ± 55 | 639 ± 29 |
| Digestive system | | | | |
| Likert scale of thirsty* | 2.1 ± 0.2$^{a}$ | 1.8 ± 0.2$^{ab}$ | 1.5 ± 0.1$^{b}$ | 1.5 ± 0.1$^{b}$ |
| Residual gastric volume*(ml) | 25.2 ± 4.6 | 29.4 ± 4.6 | 27.4 ± 4.0 | 20.9 ± 3.9 |
| Insulin resistance** | | | | |
| Change of Homa-IR[1] | 2.03 ± 1.3$^{a}$ | −0.23 ± 0.3$^{ab}$ | −0.9 ± 0.9$^{b}$ | 0.8 ± 0.7$^{ab}$ |
| Complications | | | | |
| Comprehensive Complication Index | 45.2 ± 4.5$^{a}$ | 39.7 ± 3.6$^{ab}$ | 38.5 ± 4.4$^{ab}$ | 29.6 ± 4.2$^{b}$ |
| Postoperative morbidity survey | 2.6 ± 0.2$^{a}$ | 2.5 ± 0.2$^{a}$ | 2.2 ± 0.2$^{ab}$ | 1.7 ± 0.2$^{b}$ |
| Epinephrine dose (mg) | 5.4 ± 1.4 | 2.8 ± 0.8 | 2.3 ± 1.0 | 5.1 ± 1.4 |
| Blood transfusion (ml) | 186 ± 65$^{a}$ | 125 ± 42$^{ab}$ | 65 ± 32$^{b}$ | 33 ± 19$^{b}$ |
| Change of CRP (mg/1) | −2.1 ± 1.2 | 0.9 ± 0.7 | −1.2 ± 1.1 | −0.2 ± 2.0 |
| Change of nutritional status*** | | | | |
| Nutrition Risk Screening | 0.2 ± 0.2 | 0.1 ± 0.2 | 0.4 ± 0.1 | 0.7 ± 0.2 |
| Muscle mass of mid-upper arm | 0.5 ± 0.4 | −0.2 ± 0.2 | −0.3 ± 0.3 | 0.1 ± 0.2 |

TABLE 14-continued

| Variables | Group 1 N = 36 | Group 2 N = 36 | Group 3 N = 36 | Group 4 N = 36 |
|---|---|---|---|---|
| (cm) | | | | |
| Muscle strength (kg) | −0.4 ± 1.0 | 0.0 ± 0.5 | 0.7 ± 0.7 | −0.5 ± 0.8 |
| Phage angle (°) | −0.32 ± 0.08 | −0.38 ± 0.05 | −0.32 ± 0.07 | −0.23 ± 0.09 |
| ECW/TBW[2] | 0.00 ± 0.00 | 0.00 ± 0.00 | −0.01 ± 0.00 | 0.01 ± 0.00 |
| Skeletal Muscle Index (kg/m$^2$) | −0.58 ± 0.9 | −0.28 ± 0.6 | −1.76 ± 0.7 | −0.59 ± 0.4 |
| Conut Score | 1.5 ± 0.4 | 1.7 ± 0.3 | 1.6 ± 0.3 | 1.3 ± 0.3 |
| Serum Albumin (g/dl) | −4.1 ± 0.7 | −5.8 ± 0.7 | −4.2 ± 0.5 | −4.2 ± 0.7 |
| Lymphocytes/ml | −244 ± 134$^{ab}$ | −187 ± 134$^{ab}$ | −58 ± 159$^{a}$ | −505 ± 207$^{b}$ |
| Cholesterol (mg/dl) | −0.42 ± 0.1$^{ab}$ | −0.66 ± 0.1$^{a}$ | −0.35 ± 0.09$^{b}$ | −0.44 ± 0.1$^{ab}$ |

Means ± SEM.
[1]Homeostasis Model Assessment,
[2]Extracellular Water/Total Body Water
*Before anesthesia,
**2 hours after completing operation,
***4 days after completing operation
Values not sharing a common superscript letter in the same row are significantly different at $p < 0.05$. The difference in these data among the four groups was analyzed by the Post hoc test following one-way ANOVA.

Regarding the efficacy of the intervention on the gastrointestinal tract, the fasting group had significantly more thirst than the CH loading group and ONS loading group. However, the gastric fluid volumes of the four groups were the same (Table 14). Equally important is the effect of the intervention on insulin resistance. Change of Homa-IR of CH loading Group, −0.9±0.9, was significantly lower than that of the fasting group, 2.03±1.3, p=0.026 (Table 14). The percentage of patients, who had HOMA-IR higher than 2.5 at 2 hours after stitched incision, came from the fasting group, which was significantly higher than that from the placebo group, 69% vs. 40%, p=0.016 (FIG. 1A).

Figure 1B:
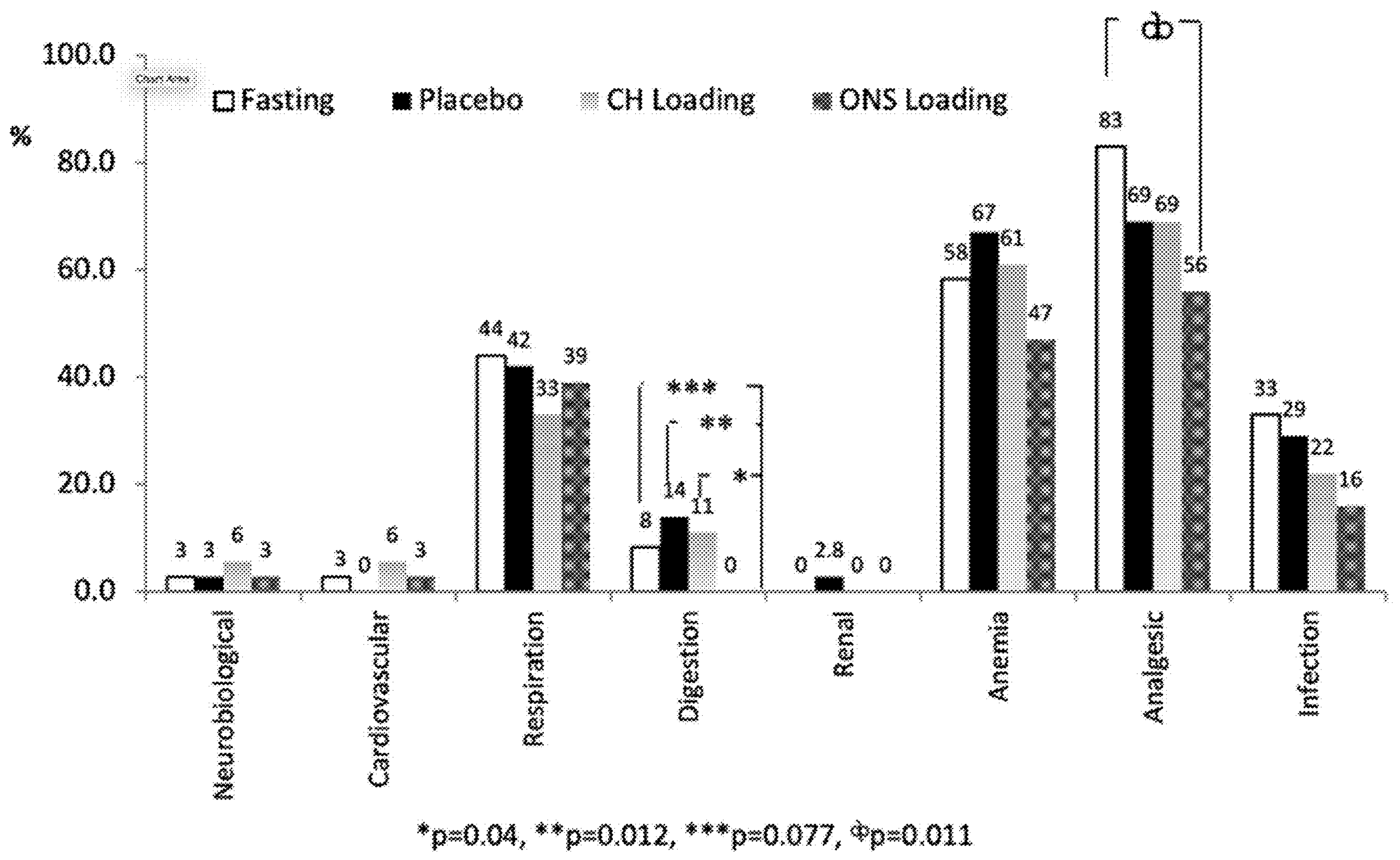
FIG. 1B depicts, in accordance with certain implementations, the percentage of patients in four groups who developed postoperative complication. Group 1 patients fasted prior to their surgery ("Fasting"). Group 2 patients drank only a placebo composition (aspartame 0.035%, 400 mL) the night before their surgery and another dose of the placebo composition (aspartame 0.035%, 200 mL) at 6:00 AM on their operation day ("Placebo"). Group 3 patients drank 400 ml of a composition comprising Maltodextrin 25% the night before their surgery followed by 200 ml of the same composition at 6:00 AM on their operation day ("CH Loading"). Group 4 patients drank the 300 ml of the disclosed nutritional composition the night before their surgery and 200 ml of the disclosed sugar solution at 6:00 AM on their operation day ("ONS Loading").

Reducing postoperative complications is the most important effect of the intervention. CCI of the ONS loading group was significantly lower than that of the fasting group, 29.6±4.2. and 45.2±4.5, respectively, p=0.01 (Table 14). Moreover, POMS of the ONS group was significantly lower than that of both fasting group, 1.7±0.2 vs. 2.6±0.2, p=0.003, and of the placebo group, 1.7±0.2 vs. 2.5±0.2, p=0.013 (Table 14). The volume of blood transfusion of ONS loading group and CH loading group was significantly lower than that of the fasting group, 33±19 vs. 186±65, p=0.013 and 65±32 vs. 186±65, p=0.049, respectively (Table 14). The frequency of patients requiring additional painkillers after surgery in the fasting group was statistically significantly higher than that of the ONS group, 83% compared to 56% (FIG. 1B). While the ONS group had no patients with postoperative gastrointestinal complications, the placebo group had 14%, the CH loading group 11%, and the fasting group 8%, the difference was statistically significant (FIG. 1B). Lastly, ONS, placebo, or CH loading did not significantly affect postoperative orthopedic surgery patients' nutrition status (Table 14). It was the same for residual gastric volume (Table 14).

The result suggested that preoperative oral administration of either a sugar solution or the combination of the nutritional composition and the sugar solution reduced the development of insulin resistance in patients undergoing orthopedic surgery. Both preoperative treatments reduced the incidence of postoperative complications, but the combination of the nutritional composition and the sugar solution was especially effective.

In places where the description above refers to particular implementations, it should be readily apparent that a number of modifications may be made without departing from the spirit thereof and that these implementations may be alternatively applied. The accompanying claims are intended to cover such modifications as would fall within the true spirit and scope of the disclosure set forth in this document. The presently disclosed implementations are, therefore, to be considered in all respects as illustrative and not restrictive, the scope of the disclosure being indicated by the appended claims rather than the foregoing description. All changes that come within the meaning of and range of equivalency of the claims are intended to be embraced therein.

What is claimed:

1. A method of reducing postoperative complications and facilitating postoperative recovery in a patient, the method consisting of: orally administering to the patient a 300 ml nutritional composition at least six (6) hours prior to surgery, wherein the nutritional composition consists of:
- soy milk;
- unsweetened whole milk;
- 0.2±0.06 g isolate milk protein/kg body weight of the patient;
- 0.1±0.04 g isolate pea protein/kg body weight of the patient;
- fiber;
- probiotic organisms consisting of at least one species of bacteria selected from the group consisting of: *Lactobacillus acidophilus, Lactobacillus reuteri, Lactobacillus casei, Bifidobacterium longum*, and *Streptococcus faecalis*; and
- a composition of vitamins and minerals consisting of 150-300 μg selenium and 300-500 μg vitamin K2, and optionally, one or more vitamins or minerals selected from the group consisting of: retinol, carotene vitamin E, vitamin D, vitamin KI, a vitamin B, vitamin C, iron, magnesium, and zinc, wherein the nutritional composition provides 0.08±0.02 g branched-chain amino acid/kg body weight of the patient; and
- orally administering to the patient a sugar solution at least two hours prior to surgery, wherein the sugar solution consists of water and a sugar, the sugar in the sugar solution provides between 0.7-1.3 g of sugar/kg body weight of the patient, and consists of 25% (w/v) maltodextrin,
- wherein the patient ingests nothing in addition to the sugar solution and water at least six (6) hours prior to the surgery, and wherein administering the nutritional composition and the sugar solution reduce the development of insulin resistance in the patient.

2. The method of claim 1, wherein the nutritional composition provides:

4.1±1.3 μg selenium/kg body weight of the patient; and
7.4±2.4 μg vitamin K2/kg body weight of the patient.

3. The method of claim 1, wherein the sugar solution consists of 50 g maltodextrin in 200 ml water.

4. The method of claim 1, wherein the patient is preparing for orthopedic surgery.

5. The method of claim 1, wherein the nutritional composition consists of:

4-8 g isolate pea protein; and
6-10 g isolate milk protein.

6. The method of claim 1, wherein the unsweetened whole milk is provided by whole milk powder and the patient is preparing for orthopedic surgery.

7. A method of reducing postoperative complications and facilitating postoperative recovery in a patient, the method consisting of: orally administering to the patient a 300 ml nutritional composition at least six (6) hours prior to surgery, wherein the nutritional composition consists of:

4-8 g isolate pea protein;
6-10 g isolate milk protein;
5.7 g fiber; and
a composition of probiotic organisms consisting of at least one species of bacteria selected from the group consisting of:
$3\times10^8$ CFUs *Lactobacillus acidophilus;*
$3\times10^8$ CFUs *Lactobacillus reuteri;*
$3\times10^8$ CFUs *Lactobacillus casei;*
$3\times10^8$ CFUs *Bifidobacterium longum;*
$3\times10^8$ CFUs *Streptococcus faecalis*; and
combinations thereof; and
orally administering to the patient a sugar solution at least two hours prior to surgery, wherein the sugar solution consists of water and sugar;
wherein the patient ingests nothing in addition to the sugar solution and water at least six (6) hours prior to the surgery, wherein the sugar in the sugar solution provides between 0.7-1.3 g of sugar/kg body weight of the patient and consists of 25% (w/v) maltodextrin.

8. The method of claim 1, wherein the patient is preparing for orthopedic surgery.

9. The method of claim 1, wherein administering the nutritional composition and the sugar solution reduces the Comprehensive Complication Index (CCI) in the patient.

10. The method of claim 1, wherein administering the nutritional composition and the sugar solution reduces Post-operative morbidity survey (POMS) score in the patient.

11. A method of reducing the development of insulin resistance in a patient preparing for surgery, the method consisting of:

orally administering to the patient a 300 ml nutritional composition at least six (6 hours prior to surgery, wherein the nutritional composition consists of:
soy milk;
unsweetened whole milk;
0.2±0.06 g isolate milk protein/kg body weight of the patient;
0.1±0.04 g isolate pea protein/kg body weight of the patient;
fiber;
probiotic organisms consisting of at least one species of bacteria selected from the group consisting of: *Lactobacillus acidophilus, Lactobacillus reuteri, Lactobacillus casei, Bifidobacterium longum*, and *Streptococcus faecalis*; and
a composition of vitamins and minerals consisting of 150-300 μg selenium and 300-500 μg vitamin K2, and optionally, one or more vitamins or minerals selected from the group consisting of: retinol, carotene vitamin E, vitamin D, vitamin K1, a vitamin B, vitamin C, iron, magnesium, and zinc; and
orally administering to the patient a sugar solution at least two hours prior to surgery, wherein the sugar solution consists of water and a sugar, the sugar in the sugar solution provides between 0.7-1.3 g of sugar/kg body weight of the patient and consists of 25% (w/v) maltodextrin,
wherein the patient ingests nothing in addition to the sugar solution and water at least six (6) hours prior to the surgery and administering the nutritional composition and the sugar solution reduce the development of insulin resistance in the patient.

* * * * *